United States Patent [19]

Barnett et al.

[11] Patent Number: 4,799,394
[45] Date of Patent: Jan. 24, 1989

[54] ANALYZER BLOCK FOR SEALING AND ISOLATING ANALYZER GAS SAMPLE FLOW

[75] Inventors: Daniel C. Barnett, Concord Twp., Lake County; George R. Hall, II, Wickliffe, both of Ohio

[73] Assignee: The Babcock & Wilcox Company, New Orleans, La.

[21] Appl. No.: 92,495

[22] Filed: Sep. 3, 1987

[51] Int. Cl.<sup>4</sup> ............................................. G01N 1/24
[52] U.S. Cl. ............................ 73/864.81; 73/864.34; 73/863.01
[58] Field of Search ............... 73/864.81, 864.34, 23, 73/863.31, 863.01; 137/312; 422/93

[56] References Cited

U.S. PATENT DOCUMENTS

| 3,794,066 | 2/1974 | Raymond | 137/312 |
| 4,134,289 | 1/1979 | Bohl et al. | 73/23 |
| 4,441,356 | 4/1984 | Bohl | 73/23 |
| 4,502,341 | 3/1985 | Hall, II | 73/864.34 |

FOREIGN PATENT DOCUMENTS 5235249 10/1978 Japan ..................... 137/312

Primary Examiner—Stewart J. Levy
Assistant Examiner—Robert P. Bell
Attorney, Agent, or Firm—Eric Marich; Vytas R. Matas; Robert J. Edwards

[57] ABSTRACT

A device for sealing and isolating analyzer gas sample flows in an aspirated sampling system is provided with a drainage channel surrounding the gas sample inlet to isolate the inlet in the plane of the sealing surface from a pressurized air supply channel in the sealing surface and intercept leakage from the air supply channel. The drainage channel is connected to a cavity via a constricted flow path to reduce leakage pressure and the cavity is vented to the environment.

10 Claims, 2 Drawing Sheets

4,799,394

ANALYZER BLOCK FOR SEALING AND ISOLATING ANALYZER GAS SAMPLE FLOW

BACKGROUND OF THE INVENTION

The present invention relates to devices for analyzing and sampling combustion gases and, more particularly, to a new and useful device for sealing and isolating aspirated gas sample flows from pressurized supply air flow.

The control of combustion systems is often dependent upon the accurate monitoring and analyzing of process gases such as combustion flue gases. Known sampling systems for measuring concentrations of oxygen carbon monoxide and other combustibles include forced or pressurized type systems and aspirated or vacuum type systems. In the pressurized systems, small amounts of leakage between the system and the environment are not critical as leakage is vented to atmosphere due to the higher sampling system pressure. In aspirated systems, however, leakage between the sampling system and environment or supply air and sampled gas channels causes the higher pressure air to flow into the sampled gas. This inflow of air increases the oxygen content of the sample and thereby results in an erroneous measurement.

The aspirators in one known arrangement, such as is disclosed in U.S. Pat. No. 4,134,289, as well as the various inlet and outlet lines associated therewith are all enclosed in a heated block to maintain the temperature well above the dew point of any sampled gases or supply air in order to prevent condensation. In the case of such high temperature analyzing, in which temperatures may exceed 450° F. (232.2° C.), metal, ceramic and asbestos materials are employed to form analyzer block parts. The contents of U.S. Pat. No. 4,134,289 are incorporated herein by reference.

The formation of fluid flow passages in the block, particularly in respect of serpentine, sinusoidally extending channels used to assure sufficient residence time to heat the fluid flows, can be facilitated by machining or otherwise forming surface grooves in a sealing face of a flat plate, such as a manifold flange, and joining the flange together with a seal plate or the like so that the adjacent surfaces establish distinct, separate flow paths. To assure adequate sealing between mating parts, however, such parts must be machined to close tolerances, be formed with microsmooth finishes and precision flatness, and then joined under high clamping loads which are uniformly distributed over the mated surfaces. In operation, small leakages may nevertheless occur due to deviations from design specifications, imperfections in the sealing surfaces such as scratches or burrs, due to dirt or particles which will sometimes get between the sealing surfaces, or even due to thermal distortion.

SUMMARY OF THE INVENTION

According to the present invention, a device for sealing and isolating analyzer gas sample flow includes a flange manifold which is provided with a drain channel circuit interposed on the sealing face between the supply air flow channel to the aspirator and the sample air flow inlets or flow passages. The drain channel circuit intercepts any leakage passing from the higher pressure air supply toward the sample air flow inlets. The drain channel includes circuits attached to large cavities that, in turn, are vented to atmosphere. The drain channel circuitry is sized to reduce the high air supply pressure to zero.

The inventive device advantageously accommodates leakage while protecting the integrity of a gas sample being analyzed.

BRIEF DESCRIPTION OF THE DRAWINGS

In the accompanying drawings, forming a part of this specification, and in which reference numerals shown in the drawings designate like or corresponding parts throughout the same.

DETAILED DESCRIPTION

Figure 1:
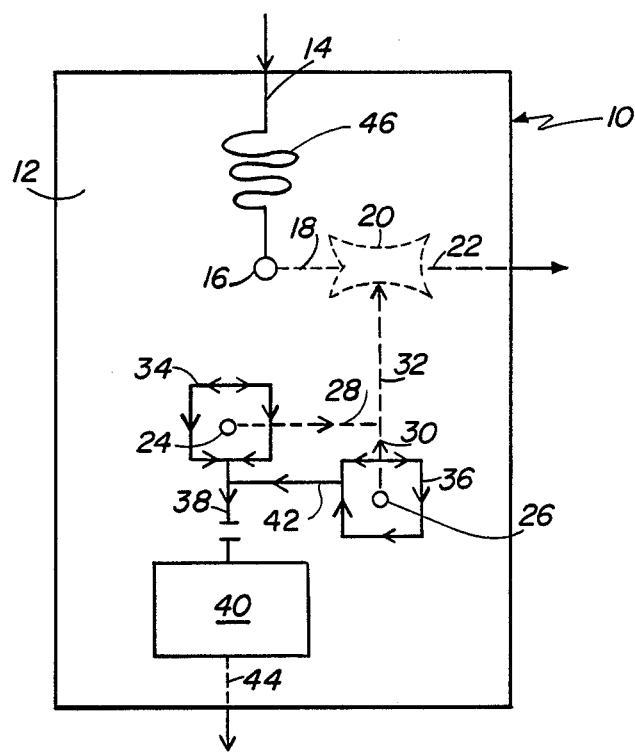
FIG. 1 is a flow diagram which schematically illustrates the aspirated flow paths of a gas analyzer and the means for isolating the aspirated flow path from leakage from the supply air flow path and ambient air in accordance with the invention.

Referring to the figures in detail, FIG. 1 provides a schematic illustration of the flow paths of an aspirated analyzer block constructed in accordance with the principles of the invention.

In FIG. 1, a flange manifold plate 10 is provided with a sealing face 12 having a series of flow paths or channels for conducting fluid there along. A first channel 14 formed in the sealing surface 12 provides a pathway for the passage of supply air along the surface of the sealing face to a opening 16 which communicates with a subsurface channel 18 formed within the flange manifold plate 10 below the sealing surface 12. The subsurface channel 18, in turn, communicates with the drive inlet connection of an aspirator 20. The aspirator 20 includes a discharge outlet channel 22.

Two sample gas inlet openings 24, 26 are provided at the sealing surface. The sample gas inlet openings 24, 26 communicate with two subsurface flow channels 28, 30, respectively. The subsurface channels 28, 30 communicate with one or more inlets 32 (only one of which is shown in FIG. 1) to the aspirator 20.

The channel means formed within the sealing surface further include drain passage channels 34 and 36 which surround the gas inlet openings 24, 26. The drain passage channels communicate with the restricted flow channels 38, 42, which in turn discharge into a cavity 40 formed within the sealing surface. The cavity 40 is connected to a vent channel 44 which is designed to discharge to atmosphere via an opening in the edge of the flange manifold plate 10. The air supply line 14 includes a section 46 formed sinusoidally within the sealing surface 12 to delay the transport time of supply air to the aspirator to thereby ensure that any air supply is properly heated by well-known means to prevent condensation. It should be understood that flow lines shown in FIG. 1 in dotted form represent channels which are not formed in the sealing surface 12 but are subsurface channels of components.

Figure 2:
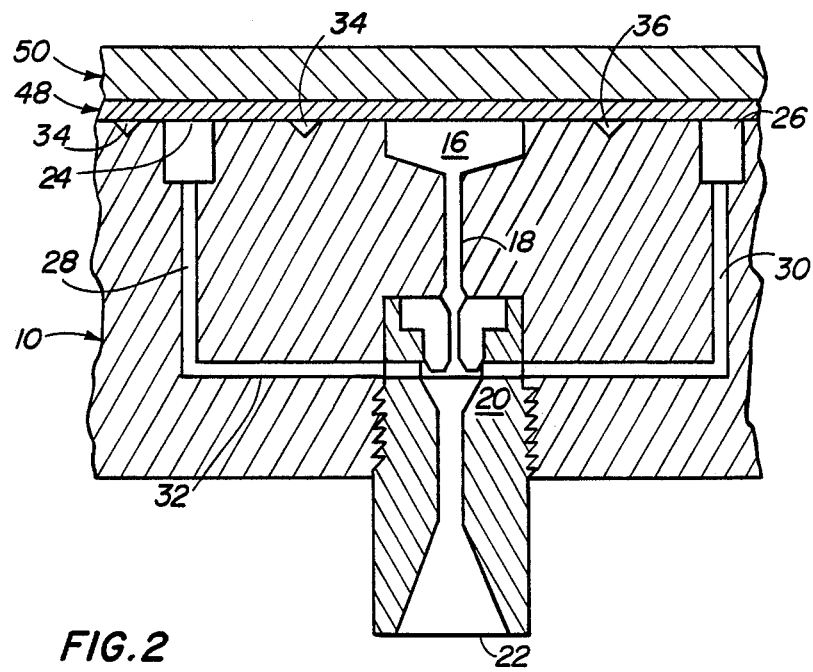
FIG. 2 is an enlarged schematic sectional view illustrating the isolation of the sample gas inlets from the air supply passage at the same plane of the sealing surface and the communication of the sample gas and air supply passage with the aspirator.

FIG. 2 illustrates a schematic cross section of a portion of the flange manifold plate 10, a sealing plate 50 and a seal 48 joined together into a rigid structure by well-known means (not shown) such as by bolting the sealing plate to the flange manifold plate 10 with the seal 48 interposed there between. The seal 48 can be the type of seal typically used for high temperature applications, for example, a crushed gasket composed of graphite.

Figure 3:
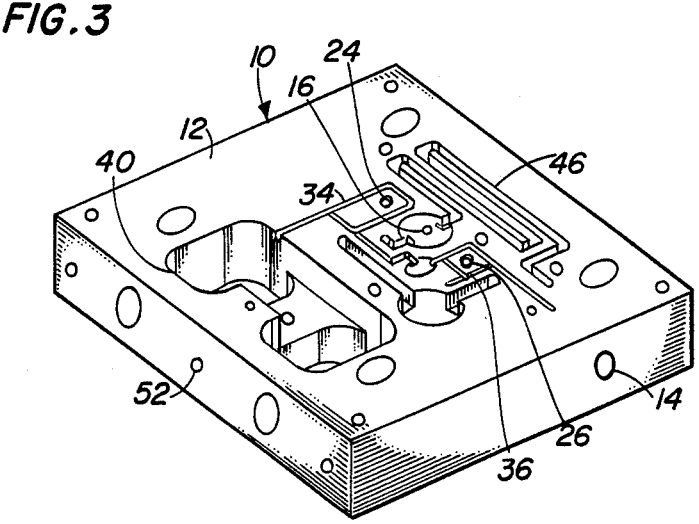
FIG. 3 is a perspective view of a flange manifold according to the invention.

Referring now to FIG. 3, there is shown a perspective view of a preferred embodiment of the flange manifold plate 10.

As best seen in FIGS. 2 and 3, the drain passage channels 34, 36 have V-shaped cross-sections and are opened to the sealing surface. The drain passage channels could also be formed with a generally U-shaped cross-section. In the embodiment of FIG. 3, the aspirator is a separate component partially housed in the flange manifold plate 10 and threadably engaged therewith.

In operation, supply air at a pressure of about 35 to 60 p.s.i.g. is provided to the aspirator 20 via the first flow channel 14 and subsurface channel 18 to establish a negative pressure at the inlet line 32 to induce a gas sample to flow under a negative pressure of up to 2.5-inch $H_2O$ (vacuum) to the aspirator 20 via inlet line 32 and through a gas analyzer (not shown) such as an oxygen analyzer or combustibles detector. The mixture of the sample gas and the supply air is discharged via the discharge outlet channel 22 typically back to the system.

In the event that the sealing surface 12 is not fully sealed, for example, due to the types of problems referred to in the background section, air from the air supply source may tend to traverse the sealing face 12 and pass into one or more of the sample gas inlet openings. However, since the inlet openings are surrounded the drain passage channels, the channels tend to intercept any such leakage flow and direct the flow to the cavity 40 via the restricted flow channel 38. The restricted flow channel 38 is sized so as to cause a full drop in supply air pressure to ambient pressure conditions as the intercepted air is passed to the cavity 40 and ultimately vented to atmosphere via vent channel 44 and an outlet 52 formed along an external surface of the flange manifold plate 10.

Certain modifications and improvements will occur to those skilled in the art upon reading the specification. As an example, individual sample gas channels may be utilized to direct sample gas to the aspirator as shown in FIG. 2 or the channels can be combined into a single line as schematically illustrated in FIG. 1. In addition, separate drain channels can be provided for each of the sample gas inlets for direct communication with the cavity 40. Alternatively, more than one cavity can be utilized. Further, it may be possible to directly abut the sealing surface of the flange manifold plate with a surface of the sealing plate without the use of a intervening sealing gasket.

The invention claimed is:

1. A device for sealing and isolating analyzer gas sample flow in a system having an aspirator, the aspirator having gas sample inlet means for drawing a sample gas flow therein and supply air inlet means, and wherein the device comprises:

a plurality of plate members joined together into a rigid structure, said plate members having sealing surfaces;

seal means for sealingly engaging the sealing surfaces of the plate members together;

at least one of said plate members including flow channel means formed in the respective sealing surface for passing fluid flow along said sealing surface, the flow channel means including an air supply passage for passing air to the aspirator supply air inlet means, the channel means further including a sample gas passage for passing gas to be sampled to the aspirator gas sample inlet means, at least a portion of the air supply passage and a portion of the sample gas passage being formed on said sealing surface at spaced locations from each other, said portion of the sample gas passage having openings in said sealing surface, and said channel means further including a drain passage having drain channels each of which encircles one of said openings of said portion of the sample gas passage in said sealing surface;

at least one of said plates including a cavity, at least one of said plates including restrictive passage means in fluid communication between the drain passage and cavity sized so as to provide a full drop in supply air pressure to ambient pressure conditions for fluid passing from the drain passage to the cavity; and outlet means for exhausting fluid from the cavity to the atmosphere.

2. A device as claimed in claim 1, wherein said portion of the sample gas passage comprises an opening in the sealing surface.

3. A device as claimed in claim 1, wherein the drain channels have a V-shaped cross-section.

4. A device as claimed in claim 1, wherein said seal means comprises a gasket interposed between the sealing surfaces.

5. A device as claimed in claim 1, wherein the outlet means comprises an outlet formed along the external surface of the plate member including the flow channel means.

6. A device as claimed in claim 1, where only one of said plate members includes the flow channel means.

7. A device as claimed in claim 2, wherein the drain passage comprises a V-shaped channel.

8. A device as claimed in claim 7, wherein said seal means comprises a gasket interposed between the sealing surfaces.

9. A device as claimed in claim 8, wherein the outlet means comprises an outlet formed along the external surface of the plate member including the flow channel means.

10. A device as claimed in claim 9, where only one of said plate members includes the flow channel means.

* * * * *